US00PP33884P2

(12) United States Plant Patent
Liu et al.

(10) Patent No.: US PP33,884 P2
(45) Date of Patent: Jan. 18, 2022

(54) ***ALPINIA* PLANT 'LY1'**

(50) Latin Name: ***Alpinia zerumbet* x *henryi***
Varietal Denomination: LY1

(71) Applicant: Foshan Lianyi Biotechnology Co., Ltd, Foshan (CN)

(72) Inventors: Wenyi Liu, Foshan (CN); Ling Lin, Foshan (CN); Nian Liu, Foshan (CN)

(73) Assignee: Foshan Lianyi Biotechnology Co., Ltd.

( * ) Notice: Subject to any disclaimer, the term of this patent is extended or adjusted under 35 U.S.C. 154(b) by 0 days.

(21) Appl. No.: 17/345,358

(22) Filed: Jun. 11, 2021

(51) Int. Cl.
*A01H 6/00* (2018.01)
*A01H 5/02* (2018.01)

(52) U.S. Cl.
USPC ..... Plt./313

(58) Field of Classification Search
USPC ..... Plt./313, 314
See application file for complete search history.

*Primary Examiner* — Annette H Para
(74) *Attorney, Agent, or Firm* — Cassandra Bright

(57) ABSTRACT

A new and distinct cultivar of *Alpinia* plant named 'LY1' is disclosed characterized by robust plants with observed resistance to ginger blast. Inflorescences are long and composed of attractive pink flowers with yellow interior petaloids. Plants have a long flowering season, of nearly 8 months, with full-flowering from June to September in Guangdong Province, China. The new variety is useful as both a cut flower and landscape plant in warm climates.

4 Drawing Sheets

Latin name of the genus and species: *Alpinia zerumbet* x *henryi*.

Variety denomination: 'LY1'.

BACKGROUND OF THE INVENTION

The new cultivar, *Alpinia* 'LY1', is the product of a planned breeding program. The intent of the breeding program was to produce new ornamental ginger varieties for both cut flower and landscape purposes with improved resistance to diseases and pests in hot, wet climates. The new variety originated from a cross pollination of an unpatented, unnamed seed parent, *Alpinia zerumbet* with the pollen parent an unpatented, unnamed variety of *Alpinia henryi*. The cross pollination was made during May of 2010 in Guangdong Province, China at a research nursery. The new cultivar 'LY1' was selected in December of 2013 at the same location.

Asexual reproduction of the new cultivar 'LY1' was first performed by division in Guangdong Province at a research nursery January of 2014. *Alpinia* 'LY1' has since produced multiple generations and has shown that the unique features of this cultivar are stable and reproduced true to type.

SUMMARY OF THE INVENTION

The cultivar 'LY1' has not been observed under all possible environmental conditions. The phenotype may vary somewhat with variations in environmentenvironmenE such as temperature, day length, and light intensity, without, however, any variance in genotype.

The following traits have been repeatedly observed and are determined to be the unique characteristics of 'LY1'. These characteristics in combination distinguish 'LY1' as a new and distinct *Alpinia* cultivar:

1. Usefulness as both a cut flower and landscape plant in warm climates.

2. Strong plants resistant to typical diseases and pests found in warm climates.
3. Ornamental flowers with pink petals and yellow interior petaloids.
4. Long inflorescences.
5. Long flowering season, of nearly 8 months, with full-flowering from June to September in Guangdong Province, China.

PARENTAL COMPARISON

Plants of the new cultivar 'LY1' are similar to plants of the seed parent in most horticultural characteristics. However, plants of the new cultivar 'LY1' differ in the following:

1. *Alpinia* 'LY1' produces inflorescences of a brighter pink, with less flowers per inflorescence.
2. *Alpinia* 'LY1' produces flowers over a longer time, approximately 8 months.
3. *Alpinia* 'LY1' produces a smaller, lighter colored fruit than the seed parent.

Plants of the new cultivar 'LY1' are similar to the pollen parent in most horticultural characteristics. However, plants of the new cultivar 'LY1' differ in the following:

1. *Alpinia* 'LY1' produces longer inflorescences, which are more drooping than those of the pollen parent.
2. Plants of *Alpinia* 'LY1' are taller than plants of the pollen parent.
3. *Alpinia* 'LY1' produces darker colored fruit than the seed parent.

COMMERCIAL COMPARISON

The new cultivar 'LY1' can be compared to the unpatented commercial variety *Alpinia zerumbet* 'Variegata'. Plants of the new cultivar 'LY1' differ in the following:

1. Plants of *Alpinia* 'LY1' are taller than plants of 'Variegata'.
2. Flowers of *Alpinia* 'LY1' are brighter pink than flowers of 'Variegata'.
3. *Alpinia* 'LY1' produces more inflorescences for cut flower purposes than 'Variegata'.
4. *Alpinia* 'LY1' produces lighter colored fruit than 'Varigata'.

BRIEF DESCRIPTION OF THE PHOTOGRAPHS

The accompanying photographs illustrate in full color typical plants of 'LY1' grown outdoors, in the ground in Guangdong Province, China. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Alpinia* plant. Temperatures ranged from approximately 2° C. to 38° C. night and day. No artificial light, photoperiodic treatments or chemical treatments were given to the plants.

DETAILED BOTANICAL DESCRIPTION

Figure 1:
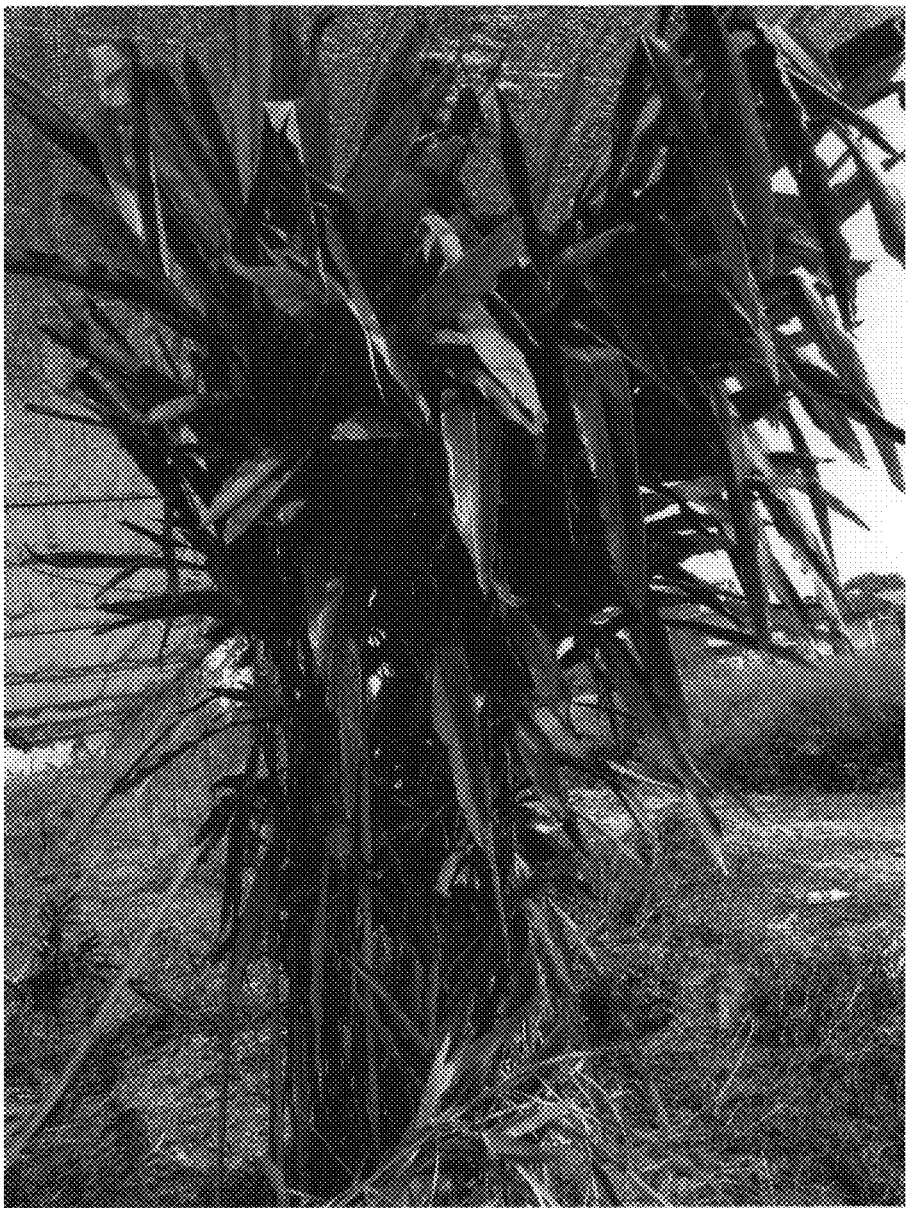
FIG. 1 illustrates in full color a typical of plant of *Alpinia* 'LY1' at approximately 12 months.
Figure 2:
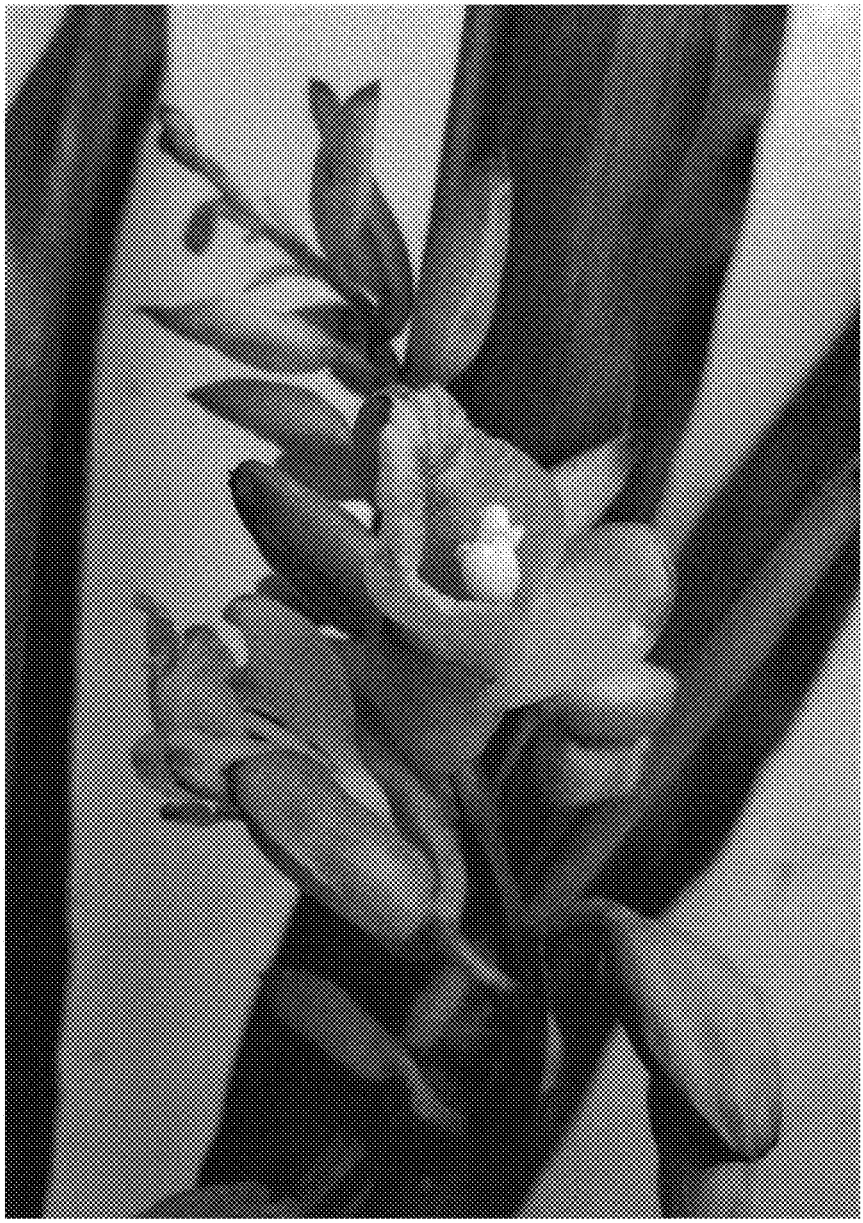
FIG. 2 illustrates in full color a typical inflorescence of *Alpinia* 'LY1'.
Figure 3:
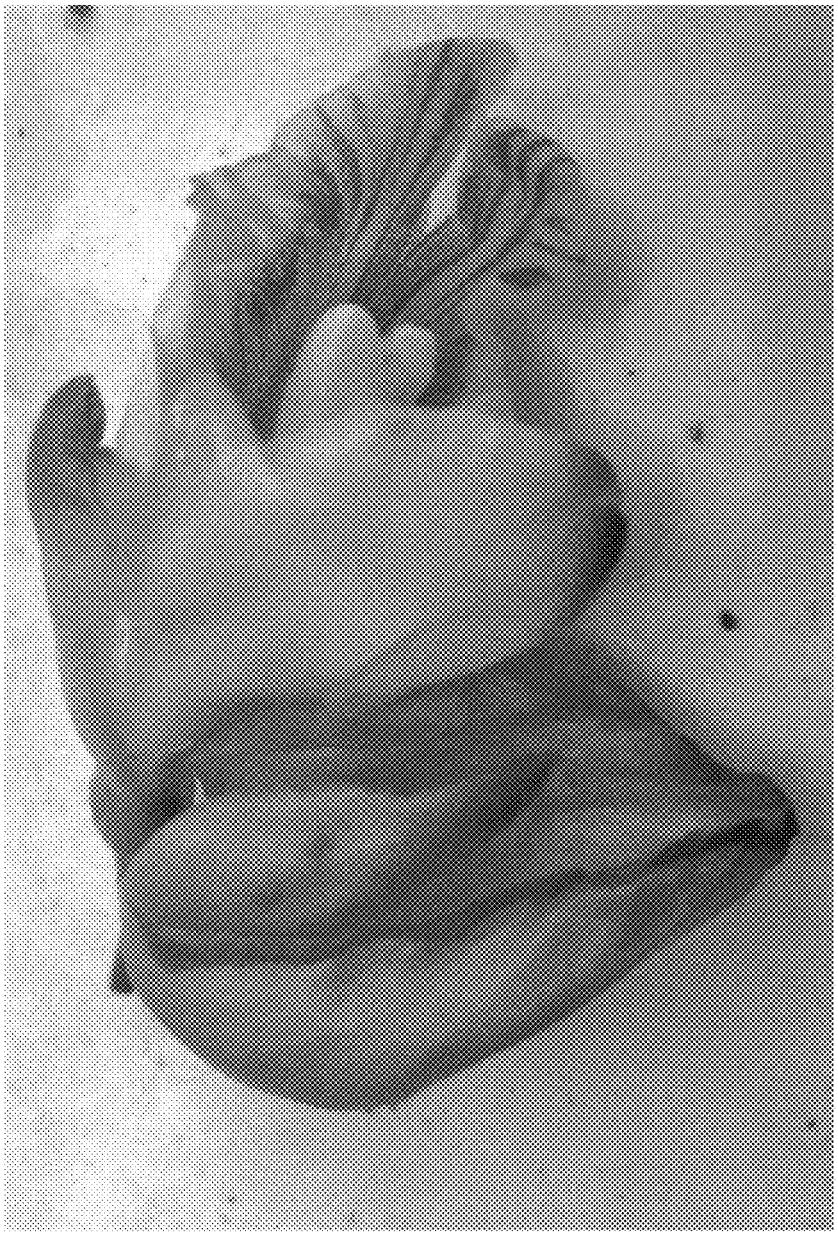
FIG. 3 illustrates in full color a typical flower of *Alpinia* 'LY1'.
Figure 4:
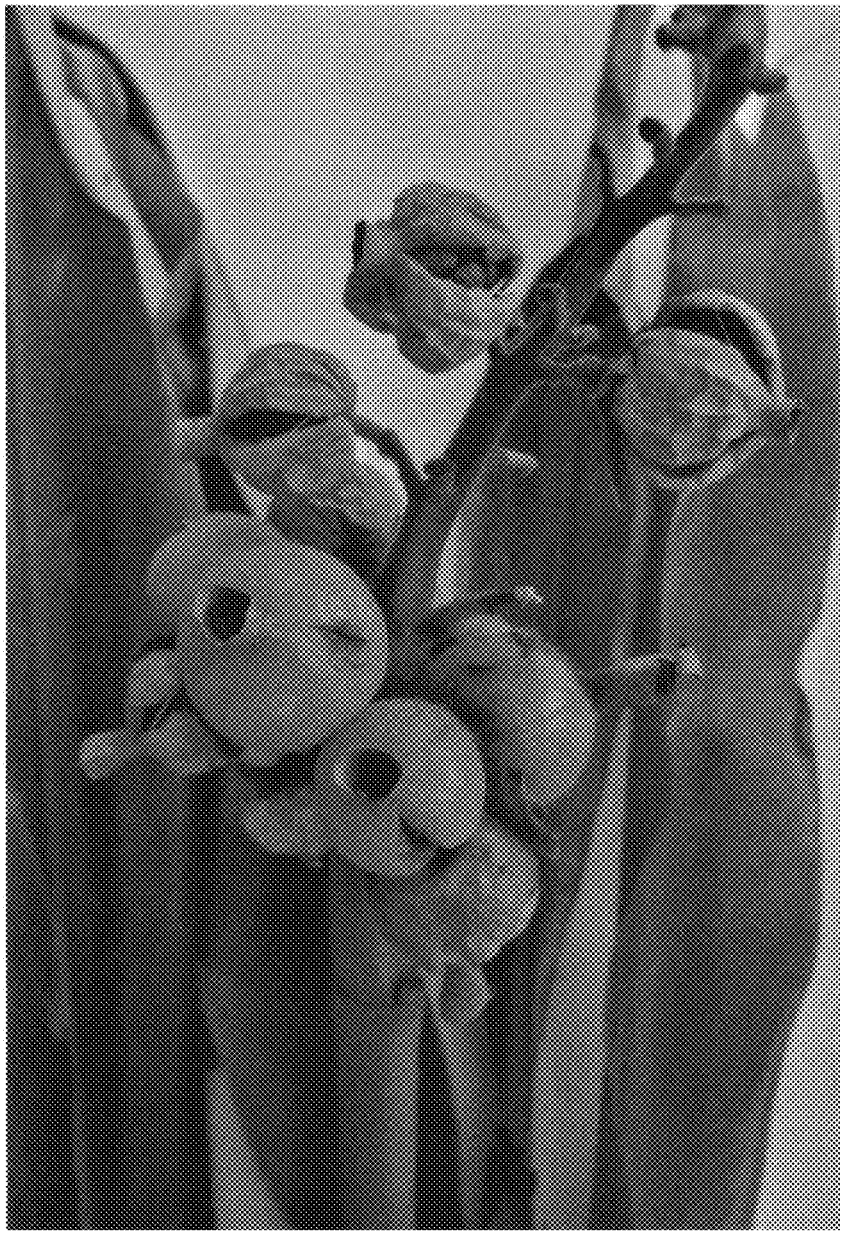
FIG. 4 illustrates in full color typical fruits of *Alpinia* 'LY1'.

In the following description, color references are made to The Royal Horticultural Society Colour Chart, 2001, except where general terms of ordinary dictionary significance are used. The following observations and measurements describe 'LY1' plants in a commercial greenhouse in Guangdong Province, China. Average day temperature was around 25° C.; average night temperature was around 18° C. No artificial light, photoperiodic treatments or chemical treatments were given to the plants. Natural light conditions were full sunlight. Measurements and numerical values represent averages of typical plant types. Measurements were taken during November of 2020.

Botanical classification: *Alpinia zerumbet* x *henryi* 'LY1'.

PROPAGATION

Type of propagation typically used: Division from side shoots.

Time to initiate roots: About 7 days at temperatures above 15° C.

PLANT

Age of plant described: Approximately 12 months.

Container size of the plant described: Field planted.

Growth habit: Tropical and subtropical perennial composed of an herbaceous pseudostem. Columnar in shape. Flowering from May until November with the most blooms occuring June through August.

Height: Average range 250 to 350 cm.

Plant spread: Approximately 85 cm.

Growth rate: Rapid.

Branching characteristics: No branching.

Root description: Cylindrical rhizomes. 30 to 50 cm long, 5 mm in diameter. Fleshy, colored near Yellow-White 158B.

FOLIAGE

Leaf:

*Arrangement.*—Alternate.
*Average length.*—Average 60 cm.
*Average width.*—8.0 cm
*Shape of blade.*—Lanceolate.
*Apex.*—Acute.
*Base.*—Cuneate.
*Margin.*—Entire, weakly undulate.
*Attachment.*—Sessile sheath.
*Texture of top surface.*—Glabrous.
*Texture of bottom surface.*—Glabrous. Main vein has a slight pubescence.
*Appearance of top surface.*—Moderate luster.
*Appearance of bottom surface.*—Matte.
*Color.*—Young foliage upper side: Near RHS Green 137C. Young foliage, under side: Near RHS Yellow-Green 146B. Mature foliage upper side: Near RHS Green 39A. Mature foliage, under side: Near RHS Yellow-Green 148D.
*Venation.*—Type: Linear. Venation color upper side: Near Green 137A. Venation color under side: Near Green 138B.

Sheath:

*Average length.*—Approximately 1 cm.
*Average diameter.*—Approximately 5 mm.
*Color.*—Upper surface: Near Green 137D. Lower surface: Near Yellow-Green 148B.
*Texture.*—Glabrous.

FLOWER

Natural flowering season: Flowering from May until November with the most blooms occurring June through August.

Inflorescence type and habit: Somewhat drooping spike, typically with 40 to 60 flowers. 3 to 6 inflorescence per plant, depending on maturity and environmental conditions. Individual flowers semi-fleshy, papilionaceous.

Inflorescence longevity as a cut flower: 4 to 5 days.

Flower longevity on plant: Individual flower 1 day.

*Total inflorescence size.*—Height: Approximately 30 cm. Width: Approximately 10 cm.
*Corolla.*—Arrangement: Papilionaceous. Longevity: 1 day. Size: Length: Approximately 4.5 to 5.0 cm. Width: Approximately 2.2 cm to 2.5 cm. Tube Length: Approximately 1.5 cm. Tube Diameter: Approximately 0.4 cm. Throat Diameter: Approximately 0.6 cm.

Petals:

*Quantity.*—3.
*Margin.*—Entire.
*Shape.*—Broad ovate.
*Apex.*—Gently tapering.
*Base.*—Truncate.
*Texture.*—Glabrous, fleshy all surfaces.
*Petal length.*—4 cm, Lip 4.5 cm.
*Petal width.*—2 cm, Lip 3.5 cm.

*Color.*—When opening: Petal color, upper surface: Red-Purple 69D. Petal color, under surface: Red-Purple 69D. Fully opened: Petal color, upper surface: Red-Purple 69D. Petal color, under surface: Red-Purple 69D. Color Changes when Aging: Near RHS Greyed-Orange 164C all surface.

*Throat color.*—Near RHS Red-Purple 69D.

*Tube color.*—Near RHS Red-Purple 69D, interior and exterior.

Interior petaloids:

*Arrangement.*—Opposite.

*Quantity.*—2.

*Length.*—2.8 cm.

*Width.*—1.3 cm.

*Shape.*—Broad deltate.

*Margin.*—Entire.

*Apex.*—Obtuse.

*Base.*—Truncate.

*Texture.*—Glabrous, fleshy all surfaces. Color: When opening: Petal color, upper surface: Yellow 11C. Petal color, under surface: Yellow 11C. Fully opened: Petal color, upper surface: Yellow 11C. Petal color, under surface: Red-Purple 69D.

Sepals:

*Quantity.*—3.

*Length.*—2.5 cm.

*Width.*—8 mm.

*Shape.*—Elongated oval.

*Apex.*—Gently tapering.

*Margin.*—Entire.

*Texture.*—Glabrous and fleshy all surfaces.

*Color.*—Upper Surface: Near Red 54C. Under Surface: Near Red 54C.

Bud: (near opening).

*Shape.*—Elongated ovate.

*Length.*—Approximately 3 cm.

*Diameter.*—Approximately 1.2 cm.

*Color.*—Near Red-Purple 65A.

Peduncle:

*Length.*—Average 1.5 cm.

*Width.*—Average 1.0 cm.

*Strength.*—Weak.

*Texture.*—Leathery.

*Color.*—Near RHS Greyed-Red 178A.

Pedicels:

*Length.*—Approximately 1.5 cm.

*Width.*—Approximately 1.0 cm.

*Strength.*—Moderately strong and flexible.

*Texture.*—Leathery.

*Color.*—Near RHS Greyed-Red 178A.

*Angle.*—Drooping 30 to 40 degrees downward.

Fragrance: Moderately pungent.

REPRODUCTIVE ORGANS

Stamens: (Androecium).

*Number.*—Average 1.

*Filament length.*—Approximately 3.0 cm.

*Filament color.*—Near RHS Yellow 11C.

*Anther length.*—0.1 cm.

*Anther color.*—Near RHS Yellow 11D.

*Anther shape.*—Elliptic.

*Pollen color.*—Near RHS Yellow 11D.

*Pollen quantity.*—Moderate.

Pistil: (Gynoecium).

*Number.*—1.

*Length.*—Approximately 2.7 cm.

*Style length.*—1 cm.

*Style color.*—Yellow 11D.

*Stigma.*—Shape: Cylindrical. Color: Near Yellow 11D. Ovary Color: Near RHS Yellow 11D.

OTHER CHARACTERISTICS

Seeds: About 50 per flower. 4 mm diameter, colored near RHS N200A.

Fruits: 40 to 50 per plant, 3.5 cm diameter, woody. Colored Orange 28A. 2. months to ripening.

Temperature tolerance: Tolerates temperatures from approximately −2° C. to at least 40° C.

Disease/pest resistance: Observed resistance to Ginger blast (*Pyricularia zingiberi*). Neither resistance nor susceptibility to other normal diseases *Alpinia* observed. Neither resistance nor susceptibility to normal pests of *Alpinia* observed.

Drought tolerance: No tolerance for drought.

What is claimed is:

1. A new and distinct cultivar of *Alpinia* plant named 'LY1' as herein illustrated and described.

* * * * *